United States Patent [19]

Revell et al.

[11] Patent Number: 6,080,712
[45] Date of Patent: Jun. 27, 2000

[54] THICKENED PERACID COMPOSITIONS

[75] Inventors: Christopher Revell, Warrington; Andrew Kevin Gray, Widnes, both of United Kingdom

[73] Assignee: Solvay Interox Limited, United Kingdom

[21] Appl. No.: 08/860,230

[22] PCT Filed: Dec. 8, 1995

[86] PCT No.: PCT/GB95/02863

§ 371 Date: Jun. 23, 1997

§ 102(e) Date: Jun. 23, 1997

[87] PCT Pub. No.: WO96/19558

PCT Pub. Date: Jun. 27, 1996

[30] Foreign Application Priority Data

Dec. 21, 1994 [GB] United Kingdom ............... 9425882

[51] Int. Cl.$^7$ .................. C11D 7/18; C11D 3/395
[52] U.S. Cl. .......... 510/372; 510/191; 510/218; 510/536; 134/3; 252/186.23; 252/186.26; 252/186.42; 422/28
[58] Field of Search .................. 510/310, 218, 510/245, 372, 191, 536; 252/186.23, 186.26, 186.42; 514/577; 134/3; 422/28

[56] References Cited

U.S. PATENT DOCUMENTS

| | | | |
|---|---|---|---|
| 3,832,234 | 8/1974 | Otrhalek et al. | 510/245 |
| 4,642,198 | 2/1987 | Humphreys et al. | 252/186.23 |
| 4,781,854 | 11/1988 | Overtonn et al. | 252/186.42 |
| 4,828,747 | 5/1989 | Rerek et al. | 252/186.26 |
| 4,929,377 | 5/1990 | Emmons et al. | 252/186.26 |
| 5,391,324 | 2/1995 | Reinhardt et al. | 252/186.26 |
| 5,409,632 | 4/1995 | Showell et al. | 252/186.23 |
| 5,419,847 | 5/1995 | Showell et al. | 510/372 |
| 5,425,898 | 6/1995 | Phillipi et al. | 252/186.26 |
| 5,451,346 | 9/1995 | Amou et al. | 252/186.23 |
| 5,489,706 | 2/1996 | Revell | 562/3 |
| 5,616,281 | 4/1997 | Hardy et al. | 510/312 |

FOREIGN PATENT DOCUMENTS

| | | |
|---|---|---|
| 0 147 207 A1 | 7/1985 | European Pat. Off. . |
| 0 188 025 A2 | 7/1986 | European Pat. Off. . |
| 0 199 385 A2 | 10/1986 | European Pat. Off. . |
| 0 201 958 | 11/1986 | European Pat. Off. . |
| 0 442 549 | 8/1991 | European Pat. Off. . |
| 0 598 170 A1 | 5/1994 | European Pat. Off. . |
| 0 598 692 A1 | 5/1994 | European Pat. Off. . |
| 0 598 694 A1 | 5/1994 | European Pat. Off. . |
| 2255507 | 11/1992 | United Kingdom . |
| WO 92/19287 | 11/1992 | WIPO . |
| WO9310088A | 5/1993 | WIPO . |
| WO 9414321A | 7/1994 | WIPO . |

OTHER PUBLICATIONS

1993 McCutcheon's vol. 1: Emulsifiers & Detergents North American Edition, (Glen Rock, NJ, copyright 1993) pp. v and 3, Jan. 1994.

Primary Examiner—Richard D. Lovering
Assistant Examiner—Daniel S Metzmaier
Attorney, Agent, or Firm—Larson & Taylor

[57] ABSTRACT

Thickened aqueous compositions comprising soluble peracids, particularly peracetic acid, are provided. The compositions are thickened by the use of one or more aliphatic alcohol ethoxylates having the general formula: $R^1R^2CH-(OCH_2CH_2)_n-OH$ in which $R^1$ and $R^2$ are each either hydrogen or linear or branched alkyl such that $R^1$ plus $R^2$ has a total of from 7 to 22 carbon atoms, and n is selected in the range of 1 to 15, such that the number ratio of carbon atoms in $R^1$ plus $R^2$:n is greater than or equal to 3:1; a co-surfactant selected from the group consisting of anionic surfactants, amine oxides, amphoteric surfactants and quaternary ammonium compounds; and one or more aliphatic alcohol ethoxylates in which the ratio of the number of carbon atoms in the alcohol moiety to the average number of ethoxylate groups is less than 3:1, and/or alkylphenol ethoxylates.

60 Claims, No Drawings

THICKENED PERACID COMPOSITIONS

This application is filed under 35 U.S.C. § 371 based on PCT/EP95/02863, filed Dec. 8, 1995.

FIELD OF THE INVENTION

The present invention relates to thickened compositions and particularly to thickened peracid compositions.

BACKGROUND OF THE INVENTION

During recent years, increasing attention has been paid by industry and the general public in Western Europe and North America to the environmental effects of the many substances that are employed in modern life. One of the classes of substances which have hitherto been widely employed comprises chlorine and oxychlorine derivatives thereof. Such compounds have been reported to generate under appropriate circumstances carcinogenic compounds and as a result, industry is seeking alternatives or replacements for such compounds in order to allay any residual public anxiety.

An alternative class of compounds comprises peroxygen compounds, of which one sub-class of especial interest comprises peracids which contain the moiety —CO—OOH. Peracids, like hydrogen peroxide, enjoy the substantial advantage of generating oxygen, either as such or in an active form during its deployment rather than chlorine or active chlorine species upon which environmentalists currently cast doubts. Furthermore, for a range of purposes such as disinfection, oxidation and bleaching, many of which are encountered domestically, peracids are more effective in general than hydrogen peroxide.

A number of the peracids are either liquid themselves or are produced conveniently in aqueous solution. Although such compositions are particularly appropriate for the treatment of or incorporation in liquid media, they are less appropriate for the treatment of solid surfaces, and particularly non-horizontal surfaces on account of the ability of liquid compositions to flow away from the point of contact. In consequence, and in order to extend the range of applications for peracids, it would be desirable to devise peracid-containing compositions that flowed less freely.

In principle, liquid compositions can be rendered less free-flowing by the incorporation of materials which thicken the liquid or introduce structure into the liquid. However, substances which have hitherto been effective thickeners for other liquids cannot be presumed automatically to be suitable for thickening liquid peracids or peracid solutions. This difficulty derives from the very same properties of the peracids that make them effective oxidising agents and bleaches. Interaction with thickeners during storage can result in the mutual decomposition of the peracid and the thickener, which in turn not only negates the beneficial effects of thickening, but also progressively removes the capability of the peracid to perform its desired task. It will be recognised that the problem is especially apparent in the case of peracids which are themselves either liquid or are present in solution. There is also a second important difficulty in attempting to thicken peracid solutions. The presence of the peracid and the corresponding carboxylic acid from which it can be derived, tends to significantly inhibit thickening. It is believed that the difficulty arises from interference of the peracid and/or carboxylic acid with aqueous structuring mechanisms which enable surfactants and like materials to thicken aqueous solutions. However, it will be understood that the instant invention does not depend upon the accuracy of the foregoing belief or explanation, but instead it relies upon the results actually demonstrated.

By comparison with soluble peracids, the problem can be somewhat less in the case of substantially insoluble solid peracids that are suspended in particulate form in aqueous media, because the peracid and the liquid constitute different physical phases that consequently minimise the extent of chemical interaction between them, and the thickening of the aqueous phase can occur with a lessened risk of interference from dissolved peracid species. European patent application No. 0 160 342 discloses that insoluble peracids can be suspended by the use of a combination of a $C_{12}$–$C_{15}$, primary alcohol ethoxylate having 7 ethylene oxides, alkylbenzene sulphonate and very high levels (>6% w/w) of an electrolyte such as sodium sulphate. European patent application No. 0 201 958 teaches that insoluble peracids can be suspended by a $C_{12}$–$C_{14}$ alcohol ethoxylate having 7.5 ethoxylates in combination with sodium dodecylbenzene sulphonate, but that the pH of these compositions must be maintained between 3.5 and 4.1, a very narrow and restrictive pH range. European patent application no 0 442 549 teaches that insoluble peracids can be suspended by $C_{12}$–$C_{15}$ alcohol ethoxylate having 3 ethoxylates in combination with a secondary alkane sulphonate and 10% w/w sodium sulphate.

It will be understood that some other potential thickeners may initially or after a brief period of storage produce a much thickened composition, but one which is rather unstable, in that its viscosity falls away rapidly from its peak. Tests employing anionic polyacrylamides fell into that category.

It will be recognised that many applications for thickened peroxygens result in the thickened compositions being discharged into a waste water system, and therefore it is desirable that the thickeners employed should posses an acceptable degree of biodegradability, and preferably the more biodegradable the thickener the better. UK patent application no. 2,255,507 discloses that a combination of a dinonylphenol ethoxylate with an amine oxide or a mixture of a fatty alcohol ethoxylate and a polyether can be employed to thicken peracetic acid solutions. However, dinonyl phenol ethoxylates are very poorly biodegradable, and are not acceptable for discharge into drainage water in many countries. The peracetic acid compositions thickened with dinonylphenolethoxylates were also found to develop a strong yellow colouration on storage, which may be unacceptable in certain potential applications.

International patent application no. WO/9424863 discloses that certain block copolymers can be employed to thicken peracetic acid solutions in which the concentration of peracetic acid is restricted to less than 0.09% by weight. The concentration of peracid in such solutions is very low, and is unsuitable for use in applications where higher concentrations of peracetic acid are required or desired.

It is an object of the present invention to seek to identify further thickening substances which are capable of thickening aqueous compositions comprising a water soluble peracid. It is a second object of some embodiments to identify further materials capable of thickening aqueous compositions comprising a water soluble peracid and obtain thereby compositions which are relatively stable chemically and physically during storage. It is a third object of a certain embodiments of the present invention to identify further materials which can thicken aqueous compositions comprising a water soluble peracid to produce viscous compositions which can be applied for disinfecting and/or cleansing purposes to non-horizontal surfaces. It is a fourth object of selected embodiments to seek to identify further thickening substances which are capable of thickening aqueous compositions comprising a water soluble peracid, and which have acceptable biodegradability. It is a fifth objective of particular embodiments of the present invention to identify a thickening system for aqueous compositions comprising a water soluble peracid which does not require the presence of high levels of electrolyte, and/or is not restricted to a very narrow pH ran and/or restricted to very dilute peracid concentrations.

SUMMARY OF THE INVENTION

According to a first aspect of the present invention there are provided thickened aqueous compositions comprising a soluble peracid in solution together with a thickener, characterised in that the thickener comprises:

(a) one or more hydrophobic aliphatic alcohol ethoxylates having the general formula:

$$R^1R^2CH—(OCH_2CH_2)_n—OH$$

in which $R^1$ and $R^2$ are each either hydrogen or linear or branched alkyl such that $R^1$ plus $R^2$ has a total of from 7 to 22 carbon atoms, and n is selected in the range of 1 to 15, such that the number ratio of carbon atoms in $R^1$ plus $R^2$: n is greater than or equal to 3:1;

(b) a co-surfactant selected from the group consisting of anionic surfactants, amine oxides, quaternary ammonium compounds and amphoteric surfactants, and (c) one or more hydrophilic aliphatic alcohol ethoxylates in which the ratio of the number of carbon atoms in the alcohol moiety to the average number of ethoxylate groups is less than 3:1, and/or alkylphenol ethoxylates, the amounts of (a), (b) and (c) above being effective to increase the viscosity of the composition.

According to a second aspect of the present invention, there is provided a process for thickening soluble peracid solutions, characterised in that the process comprises introducing into the peracid solution:

(a) one or more hydrophobic aliphatic alcohol ethoxylates having the general formula:

$$R^1R^2CH—(OCH_2CH_2)_n—OH$$

in which $R^1$ and $R^2$ are hydrogen or linear or branched alkyl such that $R^1$ plus $R^2$ has a total of from 7 to 22 carbon atoms, and n is selected in the range of 1 to 15, such that the number ratio of carbon atoms in $R^1$ plus $R^2$; n is greater than or equal to 3:1;.

(b) a co-surfactant selected from the group consisting of anionic surfactants, amine oxides, quaternary ammonium compounds and amphoteric surfactants, and (c) one or more hydrophilic aliphatic alcohol ethoxylates in which the ratio of the number of carbon atoms in the alcohol moiety to the average number of ethoxylate groups is less than 3:1, and/or alkylphenol ethoxylates, the amounts of (a), (b) and (c) above being effective to increase the viscosity of the composition.

By the use of a thickening system of the present invention it is possible to obtain solutions which are thickened and in which the peracid compound decomposes by not more than an acceptable extent during storage. In other words, the composition enjoys both physical and chemical stability.

DETAILED DESCRIPTION OF THE INVENTION

Soluble peracids which can be thickened by the thickening system of the present invention include low molecular weight aliphatic peroxyacids, for example containing up to 6 carbon atoms, of which especially preferred examples comprise peracetic acid and perpropionic acid. Other examples include perbutyric acid, percitric acid, permalic acid, perglycolic acid perlactic acid, persuccinic acid, perglutaric acid and peradipic acid. Further examples include peracids derived from monoalkylesters, and preferably monomethyl esters, of diperacids, particularly monomethylperglutarate, monmethylperadipate and monomethylpersuccinate. The compositions may alternatively include soluble aromatic peroxyacids, such monoperphthalic acid, or sulphoperbenzoic acid. A mixture of two or more peracids, particularly a mixture of persuccinic, perglutaric and peradipic acids, may be employed, if desired.

The soluble peracid may be present in a range of concentrations, subject to the requirement of total amount of acid plus peracid discussed below, for example often up to 15% and more often up to 10%. For any component, % herein is by weight based on the total weight of the composition, unless specifically stated otherwise. The lower limit is at the discretion of the user, but is normally not below 0.01%. The invention is particularly applicable to ready to use compositions containing a low concentration of peracid, and for example compositions intended for application for cleansing and/or disinfecting purposes to hard surfaces and particularly to non-horizontal surfaces. Such dilute compositions typically contain not less than 0.05%, often not less than 0.1% and more often not less than 0.5%, and often not more than 5%, more often not more than 2% by weight of peracid. For example in a number of practical embodiments the peracid content will be from 0.2%, often from 0.6%, to 1.5% by weight. It will be recognised that such compositions may contain a significant concentration of hydrogen peroxide, which may, for example, comprise from 1 to 15% of the composition, and in a number of embodiments from 3 to 10%.

Peracid compositions suitable for use in the compositions according to the present invention, and particularly those containing aliphatic peracids, are often conveniently derived by oxidation of the corresponding aliphatic carboxylic acid with aqueous hydrogen peroxide, optionally in the presence of a strong acid catalyst, and will often contain residual amounts of both the carboxylic acid and hydrogen peroxide. The total amount of peracid plus corresponding carboxylic acid is less than 30% w/w, preferably less than 25% w/w and particularly preferably 16% w/w or less. The minimum water content is usually about 50% w/w, and the water content is often greater than 60% w/w, preferably greater than about 65%. . In dilute peracid solutions, the concentration of the carboxylic acid and of hydrogen peroxide each tend to be selected in the range from 0.1% to 12%. The total concentration of carboxylic acid plus percarboxylic acid is often from 0.3 to 15%. It is often convenient to restrict the concentration of hydrogen peroxide to no greater than 7%. In many preferred compositions, equilibrium amounts of carboxylic acid, percarboxylic acid and hydrogen peroxide are present.

Hydrophobic aliphatic alcohol ethoxylates that are employed as component (a) in the thickening system according to the present invention can be derived from either primary or secondary alcohols, have the general chemical formula:

$$R^1R^2CH—(OCH_2CH_2)_n—OH$$

in which $R^1$ and $R^2$ are hydrogen or linear or branched alkyl such that $R^1$ plus $R^2$ has a total of from 7 to 22 carbon atoms, and n is selected in the range of 1 to 15, such that the number ratio of carbon atoms in $R^1$ plus $R^2$ n is greater than or equal to 3:1.

When neither $R^1$ nor $R^2$ are a hydrogen atom, i.e. the hydrophobic alcohol ethoxylate (a) is a secondary alcohol ethoxylate, $R^1$ and $R^2$ preferably have in total from 10 to 18 carbon atoms, and the number ratio of carbon atoms in $R^1$ plus $R^2$ : n is preferably in the range of from 4:1 to 7:1.

When either $R^1$ or $R^2$ is a hydrogen atom, the total number of carbon atoms is preferably from 7 to 18 carbon atoms, particularly preferably from 9 to 1 6 carbon atoms and the number ratio of carbon atoms in $R^1$ plus $R^2$:n is preferably in the range of from 4:1 to 9:1, particularly preferably from 5:1 to 8:1.

The amount of hydrophobic aliphatic alcohol ethoxylate thickener employed as component (a) is generally selected in accordance with the proportion of peracid plus carboxylic acid in the composition, for a given extent of thickening desired, although the ratio of thickener to total peracid plus acid is not necessarily linear. It is desirable to select the concentration of hydrophobic aliphatic alcohol ethoxylate (a) to be not less than 2.5%, and usually not more than 15%, and in many instances thickening of dilute peracid compositions can be achieved with quite small amounts of hydrophobic aliphatic alcohol ethoxylate, such as from 3 to 10%.

The co-surfactant (b) is selected from anionic, amine oxide, quaternary ammonium and amphoteric surfactants and mixtures thereof. The concentration of co-surfactant is normally selected to be not less than 0.1%, and often not less than 0.25%, and not more than 5%, often not more than 3%. To some extent, the amount selected depends upon the chemical nature of the co-surfactant.

Amine oxides that can be employed as co-surfactant (b) often contain from 14 to 24 carbons, including at least one long chain group, for example containing from 10 to 18 carbons and the remainder comprise short chain alkyl groups such as methyl, ethyl or propyl or hydroxyl substituted alkyl groups such as hydroxyethyl.

Anionic surfactants that can be employed as co-surfactant (b) include alkylsulphates and alkylbenzenesulphonates, which may be present either as the free acid or as an alkali metal or ammonium salt. Suitable alkylbenzenesulphonates include linear and branched alkylbenzenesulphonates, with linear alkylbenzenesulphonates being preferred. Preferably, the alkyl moiety comprises from 6 to 18 carbon atoms, and more preferably from 10 to 14 carbon atoms. The most preferred alkylbenzenesulphonate is dodecylbenzenesulphonate.

Suitable alkylsulphates include linear and branched alkylsulphates. Preferably, the alkyl moiety comprises from 6 to 18 carbon atoms, and more preferably from 8 to 14 carbon atoms. Examples of suitable alkylsulphates include sodium 2-ethylhexylsulphate and sodium laurylsulphate. A further suitable class of akylsulphates is alkyl ether sulphates wherein the sulphate group is bonded to the alkyl group via one or more, such as from 2 to 6, ethoxylate groups.

Quaternary ammonium surfactants that can be employed in as co-surfactant (b) can be represented by the general formula $R^aR^bR^cR^dN+Q-$ in which substituents $R^a$, $R^b$, $R^c$, and $R^d$ each represent an alkyl or aryl group or two of which combine with the nitrogen to form a heterocyclic nucleus, the total number of carbons in $R^a$ to $R^d$ normally comprising from about 10 to about 30 carbons, and Q represents a counterion, usually an anion which is not oxidised by peracids, such as hydroxyl, sulphate or alkyl sulphate, particularly methosulphate. One or two of the substituents normally contains from 8 to 18 linear carbons and often from C12 to C16, or forms part of the heterocyclic nucleus such as pyridinium. One of the substituents can conveniently comprise a benzyl group. The remaining substituents usually are selected from C1 to C4 alkyl groups, and especially methyl or ethyl. Preferred quaternary ammonium surfactants include alkyltrimethyl and alkylbenzyldimethyl ammonium salts.

Amphoteric surfactants that can be contemplated for use as co-surfactant (b) are generally selected to be substantially free from chloride, bromide and iodide ions because such ions can react with and decompose peracids. Amphoteric surfactants can be selected from betaines, including fatty dimethyl betaines, fatty amidopropyldimethyl betaines, fatty bishydroxyethyl betaines and fatty dimethylsulphobetaines. In some cases, the amphoteric surfactants may be defined by the general chemical formula:

where R represents an optionally substituted alkyl or aryl group, R' represents hydrogen or an optionally substituted alkyl or aryl group, and X is selected from one of the groups having the respective formulae:

Formula (1)

where m is an integer and Y represents hydrogen or a monovalent cation such as sodium, potassium or ammonium, or Formula (2)

where n is an integer, A represents a group having the formula:

where p, q and r represent integers, R" represents hydrogen or an alkyl or aryl group, and Y represents hydrogen or a monovalent cation such as sodium, potassium or ammonium, and B represents hydrogen, an alkyl or aryl group or may have the same general formula as A. In certain cases, the amphoteric surfactant has the general formula where X corresponds to formula (2) above, q is zero and B has the same general formula as A. In such amphoteric surfactants, R often contains from about 6 to about 18 carbons, and especially from about 8 to about 14 carbons and in many instances comprises a linear group. R can be synthetically derived, or can be obtained from natural sources, for example, from tallow or from coconut oil. In one particular class of amphoterics, R is derived from imidazoline.

In many embodiments of the present invention, the weight ratio of hydrophobic alcohol ethoxylate (a) to co-surfactant (b) is selected to be in the range of from 1:5 to 50:1, often from 1:2 to 30:1, and more often from 2:1 to 20:1. In certain embodiments of the present invention, good results have been achieved employing a weight ratio of hydrophobic alcohol ethoxylate (a) to co-surfactant (b) in the range of from 3:1 to 15:1, particularly from 4:1 to 10:1.

The co-surfactants of the present invention are often selected such that their biodegradability is considered acceptable in many countries for discharge into municipal effluents.

The concentration of hydrophilic alcohol ethoxylates (c) is often selected to be not less than 0.25%, and often not less than 0.5%, and not more than 10% w/w, and more often not more than 6% w/w. In certain embodiments of the present invention, good results have been achieved employing a concentration of alcohol ethoxylate (c) of from 1 to 5% w/w. Hydrophilic alcohol ethoxylates that are employed as component (c) in the thickening system include both aliphatic alcohol ethoxylates and alkylphenol ethoxylates. It will be recognised that, generally, the alkylphenol ethoxylates, for example octyl and nonylphenol ethoxylates, will be less preferred because they are currently regarded as less environmentally acceptable than aliphatic alcohol ethoxylates. Hydrophilic aliphatic alcohol ethoxylates employed as component (c) are those where the ratio of the number of carbon atoms in the alcohol moiety to the average number of ethoxylate groups is less than 3:1. The hydrophilic aliphatic alcohol ethoxylates may be derived from primary or secondary alcohols, commonly those alcohols comprising from 7 to 22, and preferably 9 to 16, carbon atoms. The number of ethoxylate groups is often in the range of from 3 to 20, and particularly in the range of from 5 to 12.

The weight ratio of hydrophobic alcohol ethoxylate (a) to hydrophilic alcohol ethoxylate (c) is often selected to be in the range of from 1:5 to 20:1, and more often from 1:2 to 10:1. In certain embodiments of the present invention, good results have been achieved employing a weight ratio of hydrophobic alcohol ethoxylate (a) to hydrophilic alcohol ethoxylate (c) in the range of from 1:1 to 6:1.

The weight ratio of hydrophobic alcohol ethoxylate (a) plus hydrophilic alcohol ethoxylate (c) to co-surfactant (b) is often selected to be in the range of from 1:1 to 50:1, and more often from 5:1 to 25:1. In certain embodiments of the present invention, good results have been achieved employing a weight ratio of hydrophobic alcohol ethoxylate (a) to hydrophilic alcohol ethoxylate (c) in the range of from 8:1 to 15:1.

The biodegradability of the alcohol ethoxylates (a) and (c) of the present invention is preferably greater than 80% as measured by OECD test 301 E and is considered acceptable in many countries for discharge into municipal effluents.

The thickened compositions according to the present invention usually have a viscosity of greater than 30 cPs, and more often greater than 50 cPs. By suitable choice of thickener system and the relative concentrations of the surfactants therein it is possible to obtain peracid compositions having a viscosity in the region of 100 to 500 cPs. Such compositions are advantageous in that they are sufficiently viscous to inhibit movement of thin layers adhering to non-horizontal surfaces, but are sufficiently fluid to enable them to be poured from bulk containers or to be ejected under pressure through nozzles. Generally, the higher the concentration of co-surfactant (b) and the higher the ratio of hydrophobic alcohol ethoxylate (a) : co-surfactant (b), the higher will be the viscosity of the composition. In some embodiments of the present invention, particularly good results have been achieved employing a concentration of co-surfactant (b) of from 0.25 to 1.5%, and a ratio of hydrophobic alcohol ethoxylate (a) : co-surfactant (b) of from 8:1 to 20:1.

It will be recognised that the viscosity of the compositions according to the present invention can be affected by factors such as the ionic strength of the composition and, particularly in the case of aliphatic peracids, by the concentration of peracid and corresponding acid in the composition. As a general rule, the higher the ionic strength of the composition and/or the concentration of peracid and corresponding aliphatic acid, the higher the concentration of alcohol ethoxylates and/or co-surfactant will need to be employed to achieve a given viscosity. In certain embodiments, the ionic strength of the composition is substantially completely derived from the peracid, hydrogen peroxide and acid equilibrium mixture, the thickening system, stabilisers for the peroxygen compound and, if present, residual acid catalyst. In other embodiments, such as in compositions which are intended for use neat or with only a small dilution in applications where lime scale removal is desirable, the peracid solution can also comprise a mineral acid, particularly phosphoric acid, often at a concentration of from about 0.5 to 5% w/w.

A further factor which may influence the viscosity of the compositions is the pH of the composition. The pH of compositions according to the present invention, including the peroxygen compounds, alcohol ethoxylate and co-surfactant and any associated stabiliser for the peroxygen compound, is in many embodiments of the present invention selected to be 0.9 or more, and commonly up to 5, although for those compositions in which a mineral acid is present, a pH of less than 0.9, such as about 0.5 or less can be selected. In many embodiments of the present invention, good results have been achieved when the pH of the thickened composition has been in the range of from 1.8 to 4, and particularly from 2 to 3.5.

In some embodiments of the present invention, the viscosity of the compositions may gradually decline on storage. In these embodiments, a substantial portion of the viscosity loss may be regained if the compositions are agitated. In other embodiments of the present invention, the gradual decline in viscosity on storage can be avoided by employing a concentration of co-surfactant (b) of 0.75% w/w or more, preferably 1% w/w or more. In certain embodiments of the present invention, compositions have been produced which are sufficiently viscous to inhibit movement of thin layers adhering to non-horizontal surfaces, but are sufficiently fluid to enable them to be poured from bulk containers or to be ejected under pressure through nozzles and possessing good viscosity stability by employing a concentration of co-surfactant (b) of from 1 to 2% w/w, a weight ratio of hydrophobic alcohol ethoxylate (a) : co-surfactant (b) of from 3:1 to 7:1 and a weight ratio of hydrophilic alcohol ethoxylate (c) : co-surfactant (b) of from 0.8:1 to 2:1.

The compositions may include one or more stabilisers for peracids and/or hydrogen peroxide so as to encourage the chemical stability of the thickened products. Known stabilisers for peroxygen compounds include aminopolycarboxylic acids, such as EDTA and DTPA, or N-heterocyclic aromatic carboxylic acids such as quinolinic acid, picolinic acid and dipicolinic acid. Particularly effective stabilisers comprise organic polyphosphonic acids, including hydroxyethylidene-diphosphonic acid and aminopolymethylene phosphonic acids. The latter often satisfy the general formula:

in which X represents —CH$_2$—PO$_3$H$_2$R represents H or the two R substituents combine to complete a cyclohexane ring, and n is an integer from 1 to 3. Examples of the formula include ethylenediaminetetra-(methylene phosphonic acid), diethylenetriaminepenta-(methylene phosphonic acid) and cyclohexanediaminetetra-(methylene phosphonic acid). A combination of any two or more of the aforementioned types of stabiliser can be employed. The weight proportion of stabilisers in the invention compositions is often up to 2%.

In addition to the foregoing components, the composition may also contain one or more perfumes and/or dyes, preferably selected at least partly on the basis of resistance to oxidation.

According to a preferred aspect of the present invention there are provided thickened aqueous compositions comprising peracetic acid in solution together with a thickener characterised in that the thickener comprises:

(a) one or more hydrophobic aliphatic alcohol ethoxylates having the general formula:

$$R^1R^2CH-(OCH_2CH_2)_n-OH$$

in which $R^1$ and $R^2$ are each either hydrogen or linear or branched alkyl such that $R^1$ plus $R^2$ has a total of from 7 to 22 carbon atoms, and n is selected in the range of 1 to 15, such that the number ratio of carbon atoms in $R^1$ plus $R^2$:n is greater than or equal to 3:1;

(b) a C8 to C14 alkylsulphate and/or C6 to C18 alkylbenzenesulphonate co-surfactant, and (c) one or more hydrophilic aliphatic alcohol ethoxylates in which the ratio of the number of carbon atoms in the alcohol moiety to the average number of ethoxylate groups is less than 3:1, the amounts of (a), (b) and (c) above being effective to increase the viscosity of the composition.

According to a particularly preferred aspect of the present invention, there are provided thickened aqueous compositions comprising peracetic acid in solution together with a thickener characterised in that the thickener comprises:

(a) one or more secondary aliphatic alcohol ethoxylates having the general formula:

$$R^1R^2CH-(OCH_2CH_2)_n-OH$$

wherein $R^1$ and $R^2$ have in total from 10 to 18 carbon atoms, and the number ratio of carbon atoms in $R^1$ plus $R^2$:n is preferably in the range of from 4:1 to 7:1.

(b) a C10 to C14 alkylbenzenesulphonate co-surfactant, and (c) one or more aliphatic alcohol ethoxylates in which the ratio of the number of carbon atoms in the alcohol moiety to the average number of ethoxylate groups is less than 3:1, the weight ratio of secondary alcohol ethoxylate (a) : co-surfactant (b) being from 2:1 to 20:1, the weight ratio of secondary alcohol ethoxylate (a) plus aliphatic alcohol ethoxylate (c): co-surfactant (b) being from 5:1 to 25:1, the concentration of secondary alcohol ethoxylate (a) being from 3 to 10% w/w, the concentration of co-surfactant (b) being from 0.25 to 3% w/w, and the concentration of aliphatic alcohol ethoxylate (c) being from 0.5 to 6% w/w.

The compositions of the present invention can be prepared by introducing the selected amount of each component in the thickening system into the aqueous solution of peracid and any residual amounts of the corresponding carboxylic acid and hydrogen peroxide, and agitating the mixture to distribute the components substantially evenly through the mixture. This can be conducted at any convenient temperature, for example at the prevailing ambient temperature which is typically in the range of from 10 to 35° C. Alternatively, the mixture may be gently heated to a temperature generally not higher than 50° C. so as to encourage rapid distribution of the components and the mixture thereafter permitted to cool to ambient.

A further method of preparing the compositions according to the present invention is to prepare a pre-mix of the hydrophobic aliphatic alcohol ethoxylate (a) with either one or both of the co-surfactant (b) and hydrophilic alcohol ethoxylate (c) surfactant, preferably with at least the co-surfactant (b), prior to the addition of the peracid solution.

It will be recognised that the peracid compositions according to the resent invention can be prepared by introducing a thickening system as herein described into a mixture of hydrogen peroxide and organic acid, optionally in the presence of a catalyst, such as a mineral acid, and allowing peracid to form in situ. This in situ preparation is applicable to the methods described in the preceding two paragraphs.

Some of the compositions of the present invention, and particularly those having a viscosity in the region of 100 to 500 cPs are intended for application domestically to surfaces, such as non-horizontal surfaces, which it is desired to disinfect and clean, thereby taking advantage of the disinfectant properties of the peroxygen compound, especially the peracid and the cleansing properties of the detergents. The peroxygen compositions when they have very high viscosities can be regarded as solids, and as such may be incorporated in particulate or granular washing or disinfecting compositions or dispersed in blocks or bars. Such blocks or bars may also incorporate substances such as waxes, either natural or synthetic polymers or very poorly soluble aliphatic carboxylic acids or poorly soluble derivatives and/or mixtures thereof which can regulate and retard the extent of contact between the peroxygen compound composition and for example a liquid medium such as flushing toilet water.

Accordingly, a further aspect of the present invention comprises the use the aforementioned invention compositions for disinfecting and cleansing by applying the composition to a hard surface and permitting contact to be maintained until at least some disinfection has occurred.

The invention compositions may be applied using conventional means and will also take into account the physical state of the composition, particularly whether it is a viscous pourable liquid or a gel. Thus, in its simplest, the compositions may be poured or smeared onto a distributor such as a cloth or sponge and applied to a receiving surface by passage of distributor across the surface. Alternatively, compositions which have a sufficiently low viscosity for them to be pourable may be forced through a distributing nozzle directly onto the receiving surface, for example by squeezing a resilient deformable storage container. Compositions in gel form may be applied by a spatula or like article or as indicated previously by incorporation in a host composition or block.

The surfaces onto which the compositions may be applied are often domestic and especially in the kitchen and other locations in which micro-organisms may be found. Suitable receptive surfaces are usually made from wood, glass, ceramics, plastic laminates and metal, and include work surfaces, sinks, pipework, walls, floors, and especially toilet bowls. It will be recognised, though, that similar potentially infected surfaces may be found in non-domestic situations, such as in commercial kitchens, food processing apparatus or containers or brewery or distillery vessels or hospitals or in animal or poultry-rearing establishments or in glass houses or other areas where the maintenance of hygienic conditions is important. The present invention includes the use of invention compositions in such non-domestic situations.

The compositions may subsequently be removed from the surfaces by water washing, possibly applied using a cloth, sponge or like article.

Having described the invention in general terms, specific embodiments thereof will now be described in greater detail by way of example only.

In the Examples below, the following abbreviations are employed:

| | |
|---|---|
| A2 | $C_{13-15}$ alcohol ethoxylate, 2 ethoxylates, commercially available in the UK from Cargo Fleet Chemicals Ltd under the trade name "SYNPERONIC A2" |
| A4 | $C_{13-15}$ alcohol ethoxylate, 4 ethoxylates, commercially available in the UK from Cargo Fleet Chemicals Ltd under the trade name "SYNPERONIC A4" |
| A9 | $C_{13-15}$ alcohol ethoxylate, 9 ethoxylates, commercially available in the UK from Cargo Fleet Chemicals Ltd under the trade name "SYNPERONIC A9" |
| 15-S-3 | $C_{15}$ secondary alcohol ethoxylate, 3 ethoxylates, commercially available in the UK from Union Carbide Chemicals Ltd under the trade name "TERGITOL 15-S-3" |
| 15-S-7 | $C_{15}$ alcohol ethoxylate, 2 ethoxylates, commercially available in the UK from Cargo Fleet Chemicals Ltd under the trade name "TERGITOL 15-S-7" |
| C12W | Cocodihydroxyethylamine oxide, commercially available in the UK from Akzo Chemicals Ltd under the trade name "AROMOX C12W". |
| LABS | C12 alkylbenzenesulphonate, sodium salt, 30% w/w solution commercially available in the UK from Cargo Fleet Chemicals under the trade name "CAFLON NAS30". |
| SLS | Sodium Laurylsulphate. |

EXAMPLES 1 to 13

In these Examples, the thickened compositions were prepared by adding each of the constituents with gentle stirring into an aqueous solution containing approximately 1% peracetic acid, 7% hydrogen peroxide and 9% acetic acid at ambient temperature (about 20–25° C.). In Examples 1 to 9, the peracetic acid solution was prepared in the absence of sulphuric acid, and had a pH of 1.9. In Examples 10 to 13, the peracetic acid solution was prepared in the presence of 0.7% sulphuric acid, and had a pH of 1.0. The percentages (w/w) of the constituents, physical appearance and the viscosities of the compositions produced (cPs, measured with a Brookfield RVT viscometer @ 50 rpm) are given in Table 1 below.

TABLE 1

Compositions and Results for Examples 1 to 13

| Example No: | 1 | 2 | 3 | 4 | 5 | 6 | 7 | 8 |
|---|---|---|---|---|---|---|---|---|
| Constituent | | | | | | | | |
| A2 | 5 | 3.6 | | | | | | |
| A4 | | | 5.4 | | | | | |
| A9 | 2.5 | 2.5 | 3.5 | 5.9 | 5.9 | 1.7 | 1 | |
| 15-S-3 | | | | 4 | 11.4 | 7.4 | 5.8 | 7.7 |
| 15-S-7 | | | | | | | | 3.5 |
| C12W | | | | | | | | |
| LABS | 3.5 | 3.5 | 3.5 | 3.5 | 3.5 | 1.7 | 1 | 3.5 |
| SLS | | | | | | | | |
| Viscosity | 224 | 44 | 64 | 36 | 3360 | 460 | 104 | 1340 |
| Appearance | o-paque | o-paque | clear | clear | clear | clear | clear | clear |

| Example No: | 9 | 10 | 11 | 12 | 13 |
|---|---|---|---|---|---|
| Constituent | | | | | |
| A2 | 9 | | | | |
| A4 | | | | | |
| A9 | 3.5 | | 3.5 | | 3.5 |
| 15-S-3 | | 9.9 | 9 | 4.1 | 4.7 |
| 15-S-7 | | 3.5 | | 3.5 | |
| C12W | | 3.5 | | | |
| LABS | 3.5 | | | 3.5 | 3.5 |
| SLS | | | 1.1 | | |
| Viscosity | 2200 | 240 | 1160 | 100 | 200 |
| Appearance | o-paque | clear | o-paque | o-paque | o-paque |

The composition prepared in Examples 5 and 6 were analysed to determine their initial peracetic acid and hydrogen peroxide concentrations, stored for 2 months at room temperature, and the viscosity and peracetic and hydrogen peroxide concentrations determined. For the composition of Example 5, the initial peracetic acid concentration was 0.67%, and that for hydrogen peroxide was 4.9%. After the 2 months storage, the viscosity measured was 1100 cPs, the concentration of peracetic acid being 0.92%, and the concentration of hydrogen peroxide 4.5%. For the composition of Example 6, the initial peracetic acid concentration was 0.85%, and that for hydrogen peroxide was 5.4%. After the 2 months storage, the viscosity measured was 448 cPs, the concentration of peracetic acid being 0.96%, and the concentration of hydrogen peroxide 5.0%.

The results of the Examples clearly showed that the thickening system according to the present invention could be employed to produce thickened peracid compositions having a wide range of viscosities. Additionally, selection of the appropriate thickening system could be employed to produce compositions having differing appearances. For example, clear compositions can be produced where clarity is desired, whereas opaque compositions can be produced for applications where this is desired, or where clarity is not essential.

The compositions were also found to exhibit shear thinning properties, which is particularly advantageous for those composition designed to be dispensed from a deformable bottle, the shear thinning nature increasing the ease with which the dispense can be achieved. This shear thinning nature is demonstrated in Examples 14 and 15. In these Examples, thickened peracetic acid compositions were prepared employing the general method of Example 1 above, except that in Example 14, the surfactants employed were 3% w/w SYNPERONIC A9, 10.5% w/w TERGITOL 15-S-3 and 3% w/w AROMOX C12W. Example 15 differed from Example 14 in that 3% w/w of TERGITOL 15-S-7 was employed in place of the SYNPERONIC A9, and that 8.4% w/w of TERGITOL 15-S-3 was employed. The viscosities of the compositions were measured using a Brookfield RVT viscometer, Spindle No. 4 at each of 100 rpm, 50 rpm, 20 rpm and 10 rpm, representing a range of shear forces. The results are given in Table 2 below.

TABLE 2

| | Viscosity (cPs) at | | | |
|---|---|---|---|---|
| Example No. | 100 rpm | 50 rpm | 20 rpm | 10 rpm |
| 14 | 940 | 1660 | 3500 | 7750 |
| 15 | 1020 | 1760 | 3600 | 7750 |

The results of Examples 14 and 15 show that as the shear (i.e. rpm) increases, so the viscosity of the compositions decreases.

EXAMPLE 16

A solution of monomethylperglutaric acid was prepared at ambient temperature by dissolving 25 g monomethylglutaric acid in 166 g demineralised water, and adding 59 g of 85% w/w hydrogen peroxide solution. To 96 g of this solution was added 2 g of SYNPERONIC A9, 8.3 g TERGITOL 15-S-3 and 2 g CAFLON NAS30. This produced a clear, thick solution having a viscosity of 450 cPs, measured with a Brookfield RVT viscometer, spindle 4@ 50 rpm.

EXAMPLE 17

A solution of percitric acid was prepared at ambient temperature by dissolving 50 g citric acid in 167.5 g demineralised water containing 2.5 g 98% w/w sulphuric acid solution, and adding 29 g of 85% w/w hydrogen peroxide solution. To 96 g of this solution was added 2 g of SYNPERONIC A9, 5.6 g TERGITOL 15-S-3 and 2 g CAFLON NAS30. This produced a clear, thick solution having a viscosity of 250 cPs, measured with a Brookfield RVT viscometer, spindle 4@ 50 rpm.

EXAMPLE 18

To 97.9 g of an aqueous solution containing approximately 1 % peracetic acid, 7% hydrogen peroxide and 9% acetic acid at ambient temperature (about 20–25° C.) was added 2.2 g of 90% w/w aqueous phosphoric acid solution, 3 g CAFLON NAS30, 3 g SYNPERONIC A9 and 5.77 g TERGITOL 15-S-3. This produced a thick solution having a viscosity of 240 cPs, measured with a Brookfield RVT viscometer, spindle 4@ 50 rpm.

EXAMPLES 19 to 24

A stock solution was prepared by mixing 477.5 g of an aqueous solution containing approximately 1 % peracetic acid, 7% hydrogen peroxide and 9% acetic acid at ambient temperature (about 20–25° C.) 11.15 g CAFLON NAS30, and 11.25 g SYNPERONIC A9. In Example 19, to 96.3 g of the stock solution was added, with stirring, 6 g TERGITOL 15-S-3 and 4 g of a 30% w/w sodium xylene sulphonate solution to produce a composition having a viscosity of 224 cPs measured with a Brookfield RVT viscometer, spindle 4@ 50 rpm. In Example 20, to 96 g of the stock solution was added, with stirring, 6 g TERGITOL 15-S-3 and 1.1 g of polypropylene glycol (Mol Wt 425) to produce a clear composition having a viscosity of 344 cPs measured with a Brookfield RVT viscometer, spindle 4@ 50 rpm. In Example 21, to 96 g of the stock solution was added, with stirring, 6 g TERGITOL 15-S-3 and 2 g of polyethylene glycol (Mol Wt 200) to produce a composition having a viscosity of 560 cPs measured with a Brookfield RVT viscometer, spindle 4@ 50 rpm. In Example 22, to 95.2 g of the stock solution was added, with stirring, 6 g TERGITOL 15-S-3 and 1 g of polyethylene glycol (Mol Wt 300) to produce a composition having a viscosity of 520 cPs measured with a Brookfield RVT viscometer, spindle 4@ 50 rpm. In Example 23, to 97.3 g of the stock solution was added, with stirring, 6 g TERGITOL 15-S-3 and 1.6 g of polyethylene glycol (Mol Wt 600) to produce a composition having a viscosity of 448 cPs measured with a Brookfield RVT viscometer, spindle 4@ 50 rpm. In Example 24, to 96 g of the stock solution was added, with stirring, 6 g TERGITOL 15-S-3 and 1 g of polyethylene glycol (Mol Wt 8000) to produce a composition having a viscosity of 544 cPs measured with a Brookfield RVT viscometer, spindle 4@ 50 rpm.

EXAMPLE 25

To 3538 g of an aqueous solution containing approximately 1% peracetic acid, 7% hydrogen peroxide and 9% acetic acid at ambient temperature (about 20–25° C.) was added 73.2 g CAFLON NAS30, 73.2 g SYNPERONIC A9, 296 g TERGITOL 15-S-3 and 20 g of perfume. This produced a thick solution having a viscosity of 104 cPs, measured with a Brookfield RVT viscometer, spindle 4@ 50 rpm. On storage at ambient temperature for 1 week, the viscosity of the solution had reduced to 24 cPs. To 400 g of this solution was added with stirring a further 10 g CAFLON NAS 30. The solution so produced had a viscosity of 200 cPs. After 10 days storage, this had risen to 480 cPs.

EXAMPLE 26

To 96.5 g of the stock solution employed in Examples 19 to 24 was added aliquots of TERGITOL 15-S-3. After each addition of TERGITOL 15-S-3, the viscosity was measured with a Brookfield RVT viscometer, spindle 4@ 50 rpm, and the appearance of the solution noted. The results were as listed below.

| Weight TERGITOL 15-S-3 added, g | Viscosity, cPs | Appearance |
| --- | --- | --- |
| 5.2 | 72 | translucent/white |
| 5.8 | 488 | translucent/clear |
| 6.1 | 584 | translucent/clear |
| 6.4 | 688 | translucent/clear |
| 6.9 | 900 | translucent/clear |
| 7.2 | 1020 | translucent/clear |
| 7.5 | 940 | clear |
| 8 | 1260 | clear |
| 8.7 | 1700 | clear |
| 9.2 | 1750 | clear |
| 10.2 | 60 | clear |

What is claimed is:

1. Thickened aqueous compositions comprising 0.01 to 15% by weight of a water soluble peracid in solution together with a thickener wherein the thickener comprises:
   (a) one or more secondary aliphatic alcohol ethoxylates having the general formula:
   $R^1R^2$—CH—$(OCH_2CH_2)_n$—OH
   wherein $R^1$ and $R^2$ are each either hydrogen or linear or branched alkyl such that $R^1$ plus $R^2$ has a total of 7 to 22 carbon atoms and n is selected in the range of 1 to 15, and the number ratio of carbon atoms in $R^1$ plus $R^2$:n is in the range of from 4:1 to 7:1;
   (b) a C10 to C14 alkylbenzenesulphonate co-surfactant, and
   (c) one or more aliphatic alcohol ethoxylates in which the ratio of the number of carbon atoms in the alcohol moiety to the average number of ethoxylate groups is less than 3:1, the weight ratio of secondary alcohol ethoxylate (a):co-surfactant (b) being from 1:1 to 20:1, the weight ratio of secondary alcohol ethoxylate (a) plus aliphatic alcohol ethoxylate (c):co-surfactant (b) being from 1:1 to 25: 1, the concentration of secondary alcohol ethoxylate (a) being from 3 to 15% w/w, the concentration of co-surfactant (b) being from 0.25 to 5% w/w, and the concentration of aliphatic alcohol ethoxylate (c) being from 0.5 to 6% w/w.

2. A composition according to claim 1, wherein the co-surfactant (b) comprises dodecylbenzenesulphonate.

3. A composition according to claim 1 having a viscosity of greater than 30 cPs.

4. A composition according to claim 1, having a pH of from 0.9 to 5.

5. A composition according to claim 1, wherein the total amount of peracid plus corresponding carboxylic acid in the peracid composition is less than 30% w/w.

6. A composition according to claim 1, wherein the concentration of peracid is from 0.05 to 5% by weight.

7. A composition according to claim 1, wherein the peracid solution is substantially free from mineral acid.

8. A composition according to claim 1, wherein the aqueous peracid solution contains from 0.1 to 15% by weight of a water-soluble peracid.

9. A composition according to claim 1, wherein the number ratio of carbon atoms in $R^1$ and $R^2$: n is in the range of from 5:1 to 7:1.

10. A composition according to claim 1, wherein the total number of carbon atoms is from 9 to 16 carbon atoms.

11. A composition according to claim 1, wherein the soluble peracid comprises peracetic acid.

12. A composition according to claim 1, wherein the weight ratio of hydrophobic alcohol ethoxylate (a) to co-surfactant (b) is in the range of from 2:1 to 20:1.

13. A composition according to claim 1, wherein the weight ratio of hydrophobic alcohol ethoxylate (a) to co-surfactant (b) is in the range of from 4:1 to 10:1.

14. A composition according to claim 1, wherein the weight ratio of hydrophobic alcohol ethoxylate (a) to hydrophylic alcohol ethoxylate (c) is in the range of from 1:5 to 20:1.

15. A composition according to claim 1, wherein the weight ratio of hydrophobic alcohol ethoxylate (a) to hydrophylic alcohol ethoxylate (c) is in the range of from 1:1 to 6:1.

16. A composition according to claim 1, wherein the weight ratio of hydrophobic alcohol ethoxylate (a) plus hydrophylic alcohol ethoxylate (c) to co-surfactant (b) is in the range of from 5:1 to 25:1.

17. A composition according to claim 1, wherein the weight ratio of hydrophobic alcohol ethoxylate (a) plus hydrophylic alcohol ethoxylate (c) to co-surfactant (b) is in the range of from 8:1 to 15:1.

18. A composition according to claim 1, wherein the concentration of co-surfactant (b) is from 0.25 to 1.5% and the ratio of hydrophobic alcohol ethoxylate (a):co-surfactant (b) is from 8:1 to 20:1.

19. A composition according to claim 1, wherein the concentration of peracid is from 0.01 to 2% by weight.

20. A composition according to claim 1, wherein $R^1$ and $R^2$ have in total from 10 to 18 carbon atoms.

21. A process for thickening an aqueous peracid solution containing 0.01 to 15% by weight of a water soluble peracid, comprising introducing into said peracid solution:

(a) one or more secondary aliphatic alcohol ethoxylates having the general formula:

$R^1R^2CH—(OCH_2CH_2)_n—OH$ wherein $R^1$ and $R^2$ are each either hydrogen or linear or branched alkyl such that $R^1$ plus $R^2$ has a total of 7 to 22 carbon atoms, and n is selected in the range of 1 to 15, and the number ratio of carbon atoms in $R^1$ plus $R^2$:n is in the range of from 4:1 to 7:1;

(b) a C10 to C14 alkylbenzenesulphonate co-surfactant, and (c) one or more aliphatic alcohol ethoxylates in which the ratio of the number of carbon atoms in the alcohol moiety to the average number of ethoxylate groups is less than 3:1, the weight ratio of secondary alcohol ethoxylate (a):co-surfactant (b) being from 1:1 to 20: 1, the weight ratio of secondary alcohol ethoxylate (a) plus aliphatic alcohol ethoxylate (c):co-surfactant (b) being from 1:1 to 25:1, the concentration of secondary alcohol ethoxylate (a) being from 3 to 15% w/w, the concentration of co-surfactant (b) being from 0.25 to 5% w/w, and the concentration of aliphatic alcohol ethoxylate (c) being from 0.5 to 6% w/w.

22. A process according to claim 21, wherein the viscosity of the composition is greater than 30 cPs.

23. A process according to claim 21, wherein the pH of the composition is from 0.9 to 5.

24. A process according to claim 21, wherein the total amount of peracid plus corresponding carboxylic acid in the peracid composition is less than 30% w/w.

25. A process according to claim 21, wherein the concentration of peracid is from 0.05 to 5% by weight.

26. A process according to claim 21, wherein the peracid solution is substantially free from mineral acid.

27. A process according to claim 21, wherein the total amount of peracid plus corresponding carboxylic acid in the peracid composition is less than 16% w/w.

28. A process according to claim 21, wherein the aqueous peracid solution contains from 0.1 to 15% by weight of a water-soluble peracid.

29. A process according to claim 21, wherein the number ratio of carbon atoms in $R^1$ and $R^2$: n is in the range of from 5:1 to 7:1.

30. A process according to claim 21, wherein the total number of carbon atoms is from 9 to 16 carbon atoms.

31. A process according to claim 21, wherein the soluble peracid comprises peracetic acid.

32. A process according to claim 21, wherein the weight ratio of hydrophobic alcohol ethoxylate (a) to co-surfactant (b) is in the range of from 2:1 to 20:1.

33. A process according to claim 21, wherein the weight ratio of hydrophobic alcohol ethoxylate (a) to co-surfactant (b) is in the range of from 4:1 to 10:1.

34. A process according to claim 21, wherein the weight ratio of hydrophobic alcohol ethoxylate (a) to hydrophylic alcohol ethoxylate (c) is in the range of from 1:5 to 20:1.

35. A process according to claim 21, wherein the weight ratio of hydrophobic alcohol ethoxylate (a) to hydrophylic alcohol ethoxylate (c) is in the range of from 1:1 to 6:1.

36. A process according to claim 21, wherein the weight ratio of hydrophobic alcohol ethoxylate (a) plus hydrophylic alcohol ethoxylate (c) to co-surfactant (b) is in the range of from 5:1 to 25:1.

37. A process according to claim 21, wherein the weight ratio of hydrophobic alcohol ethoxylate (a) plus hydrophylic alcohol ethoxylate (c) to co-surfactant (b) is in the range of from 8:1 to 15:1.

38. A process according to claim 21, wherein the concentration of co-surfactant (b) is from 0.25 to 1.5% and the ratio of hydrophobic alcohol ethoxylate (a):co-surfactant (b) is from 8:1 to 20: 1.

39. A process according to claim 21, wherein the concentration of peracid is from 0.01 to 2% by weight.

40. A process according to claim 21, wherein $R^1$ and $R^2$ have in total from 10 to 18 carbon atoms.

41. A method for cleaning and/or disinfecting hard surfaces, comprising contacting a hard surface with a thickened aqueous composition comprising 0.01 to 15% by weight of a water soluble peracid in solution together with a thickener wherein the thickener comprises:

(a) one or more secondary aliphatic alcohol ethoxylates having the general formula:

$R^1R^2CH—(OCH_2CH_2)_n—OH$ wherein $R^1$ and $R^2$ are each either hydrogen or linear or branched alkyl such that $R^1$ plus $R^2$ has a total of 7 to 22 carbon atoms, and n is selected in the range of 1 to 15, and the number ratio of carbon atoms in R' plus $R^2$:n is in the range of from 4:1 to 7:1;

(b) a C10 to C14 alkylbenzenesulphonate co-surfactant, and (c) one or more aliphatic alcohol ethoxylates in which the ratio of the number of carbon atoms in the alcohol moiety to the average number of ethoxylate groups is less than 3:1, the weight ratio of secondary alcohol ethoxylate (a):co-surfactant (b) being from 1:1 to 20: 1, the weight ratio of secondary alcohol ethoxylate (a) plus aliphatic alcohol ethoxylate (c):co-surfactant (b) being from 1:1 to 25:1, the concentration of secondary alcohol ethoxylate (a) being from 3 to 15% w/w, the concentration of co-surfactant (b) being from 0.25 to 5% w/w, and the concentration of aliphatic alcohol ethoxylate (c) being from 0.5 to 6% w/w.

42. A method according to claim 41, wherein the viscosity of the composition is greater than 30 cPs.

43. A composition according to claim 41, wherein the pH of the composition is from 0.9 to 5.

44. A method according to claim 41, wherein the total amount of peracid plus corresponding carboxylic acid in the peracid composition is less than 30% w/w.

45. A method according to claim 41, wherein the concentration of peracid is from 0.05 to 5% by weight.

46. A method according to claim 41, wherein the peracid solution is substantially free from mineral acid.

47. A method according to claim 41, wherein the total amount of peracid plus corresponding carboxylic acid in the peracid composition is less than 16% w/w.

48. A method according to claim 41, wherein the aqueous peracid solution contains from 0.1 to 15% by weight of a water-soluble peracid.

49. A method according to claim 41, wherein the number ratio of carbon atoms in $R^1$ and $R^2$: n is in the range of from 5:1 to 7:1.

50. A method according to claim 41, wherein the total number of carbon atoms is from 9 to 16 carbon atoms.

51. A method according to claim 41, wherein the soluble peracid is peracetic acid.

52. A method according to claim 41, wherein the weight ratio of hydrophobic alcohol ethoxylate (a) to co-surfactant (b) is in the range of from 2:1 to 20:1.

53. A method according to claim 41, wherein the weight ratio of hydrophobic alcohol ethoxylate (a) to co-surfactant (b) is in the range of from 4:1 to 10:1.

54. A method according to claim 41, wherein the weight ratio of hydrophobic alcohol ethoxylate (a) to hydrophylic alcohol ethoxylate (c) is in the range of from 1:5 to 20:1.

55. A method according to claim 41, wherein the weight ratio of hydrophobic alcohol ethoxylate (a) to hydrophylic alcohol ethoxylate (c) is in the range of from 1:1 to 6:1.

56. A method according to claim 41, wherein the weight ratio of hydrophobic alcohol ethoxylate (a) plus hydrophylic alcohol ethoxylate (c) to co-surfactant (b) is in the range of from 5:1 to 25:1.

57. A method according to claim 41, wherein the weight ratio of hydrophobic alcohol ethoxylate (a) plus hydrophylic alcohol ethoxylate (c) to co-surfactant (b) is in the range of from 8:1 to 15:1.

58. A method according to claim 41, wherein the concentration of co-surfactant (b) is from 0.25 to 1.5% and the ratio of hydrophobic alcohol ethoxylate (a):co-surfactant (b) is from 8:1 to 20:1.

59. A method according to claim 41, wherein the concentration of peracid is from 0.01 to 2% by weight.

60. A method according to claim 41, wherein $R^1$ and $R^2$ have in total from 10 to 18 carbon atoms.

* * * * *